US012631611B2

(12) United States Patent
Ito

(10) Patent No.: US 12,631,611 B2
(45) Date of Patent: May 19, 2026

(54) METHOD FOR ASSESSING AROMA COMPONENT AND METHOD FOR PREPARING FLAVOR COMPOSITION

(71) Applicant: Takasago International Corporation, Tokyo (JP)

(72) Inventor: Shinichiro Ito, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 517 days.

(21) Appl. No.: 18/268,829

(22) PCT Filed: Dec. 20, 2021

(86) PCT No.: PCT/JP2021/046923
§ 371 (c)(1),
(2) Date: Jun. 21, 2023

(87) PCT Pub. No.: WO2022/138527
PCT Pub. Date: Jun. 30, 2022

(65) Prior Publication Data
US 2024/0044859 A1 Feb. 8, 2024

(30) Foreign Application Priority Data
Dec. 24, 2020 (JP) .............................. JP2020-215140

(51) Int. Cl.
*G01N 33/02* (2006.01)
*A23L 2/56* (2006.01)
(Continued)

(52) U.S. Cl.
CPC ................ *G01N 33/02* (2013.01); *A23L 2/56* (2013.01); *A23L 27/2024* (2016.08);
(Continued)

(58) Field of Classification Search
CPC .. G01N 33/02; G01N 33/497; G01N 33/4975; A23L 2/56; A23L 27/2024;
(Continued)

(56) References Cited

U.S. PATENT DOCUMENTS

| | | |
|---|---|---|
| 2014/0220195 A1 | 8/2014 | Kohn et al. |
| 2017/0273596 A1 | 9/2017 | Le Reverend et al. |
| 2022/0187261 A1 | 6/2022 | Takagaki et al. |

FOREIGN PATENT DOCUMENTS

| | | |
|---|---|---|
| GB | 2 494 862 A | 3/2013 |
| JP | 2007-236233 A | 9/2007 |

(Continued)

OTHER PUBLICATIONS

Rui et al., "Technology of integrated evaluation of food aroma," Science and Technology of Food Industry, 2008, 29(7):277-279, with English abstract.
(Continued)

*Primary Examiner* — Laura Martin
*Assistant Examiner* — Anthony W Megna Fuentes
(74) *Attorney, Agent, or Firm* — Foley & Lardner LLP

(57) ABSTRACT

The present invention relates to a method for assessing an aroma component that can be added to a food or beverage product, and a method for preparing a flavor composition comprising adjusting a blending ratio of an aroma component on the basis of the assessing method. In the present invention, a change in concentration of each aroma component with respect to a number of breaths (t) during a breath cycle is measured; an area under a curve value (a value) per unit amount for a first breath and a coefficient (b value) indicating a degree of attenuation of the area under the curve value are respectively calculated; and the influence on flavor of the aroma component contained in the food or beverage product is evaluated by using the magnitude relationships of
(Continued)

the a value and the b value of the two or more types of aroma components.

6 Claims, 3 Drawing Sheets

(51) Int. Cl.

| | | |
|---|---|---|
| A23L 27/00 | (2016.01) | |
| A23L 27/20 | (2016.01) | |
| G01N 33/497 | (2006.01) | |

(52) U.S. Cl.
CPC ........... *A23L 27/203* (2016.08); *A23L 27/204* (2016.08); *A23L 27/2056* (2016.08); *G01N 33/497* (2013.01); *G01N 33/4975* (2024.05)

(58) Field of Classification Search
CPC .. A23L 27/203; A23L 27/204; A23L 27/2056; A23L 27/00
See application file for complete search history.

(56) References Cited

FOREIGN PATENT DOCUMENTS

| JP | 2009-031138 A | 2/2009 |
|---|---|---|
| JP | 2016-045156 A | 4/2016 |
| JP | 2017-525504 A | 9/2017 |
| JP | 2018-072210 A | 5/2018 |
| JP | 2018-141741 A | 9/2018 |
| JP | 2018-185187 A | 11/2018 |
| JP | 2019-045243 A | 3/2019 |
| JP | 2020-016503 A | 1/2020 |
| JP | 2020-134145 A | 8/2020 |
| TW | 201733459 A | 10/2017 |

OTHER PUBLICATIONS

Heenan et al., "PTR-TOF-MS monitoring of in vitro and in vivo flavour release in cereal bars with varying sugar composition," Food Chemistry, Sep. 6, 2011, 131(2):477-484.
Hodgson et al., "Aroma Release and Delivery Following the Consumption of Beverages," J. Agric. Food Chem., 2005, 53:1700-1706.
Omori et al., "Approaches for flavor analysis during food intake," The Koryo, Dec. 20, 2017, 276:61-71, with English abstract.

METHOD FOR ASSESSING AROMA COMPONENT AND METHOD FOR PREPARING FLAVOR COMPOSITION

CROSS-REFERENCE TO RELATED APPLICATIONS

This application is the U.S. National Stage of PCT/JP2021/046923, filed Dec. 20, 2021, which claims priority to JP 2020-215140, filed Dec. 24, 2020.

TECHNICAL FIELD

The present invention relates to a method for evaluating aroma components that can be added to a food or beverage product, and to a method for preparing a flavor composition, the method including a step of adjusting a blending ratio of the aroma components based on the evaluation.

BACKGROUND ART

The flavor industry needs to develop flavors that fit consumer preferences and product design. For example, in order to develop a flavor that satisfies the requirements when used in a food or beverage product, it is important to understand the characteristics of a retronasal aroma that contributes significantly to the aromatic impression perceived when consuming the food or beverage product. Conventionally, flavors have been characterized by the experience and sensory findings of skilled flavorists, but this has presented a challenge in terms of objectivity.

There is a report of an effort to express retronasal aroma behavior in a mathematical formula regarding only two flavor compounds in beverage water (see Non-patent literature 1). However, the literature mainly focuses on the influence of the presence or absence of a lipid in the beverage water on the coefficient in the formula, and does not refer to the preparation of a flavor composition.

In addition, a method has been reported for evaluating the expression characteristics (initial onset or persistence) of aromas of various flavor compounds in the oral cavity in a simple, objective, and efficient manner without relying on the experience of flavorists as previously (see Patent literature 1). Furthermore, a method has been reported for searching for a useful flavor compound to reproduce the expression of a favorable lingering aroma in beverages in a simple, objective, and efficient manner without relying on the experience and trial-and-error of flavorists as previously (see Patent literature 2).

However, in both reports, the method of calculating an objective index and the method of searching using an adsorbent are based on inventors' original techniques, and both methods target a limited range of product forms, so they cannot be said to be methods for preparing a flavor composition for a food or beverage product based on an objective evaluation of the retronasal aroma behavior when the food or beverage product is consumed.

On the other hand, as an attempt to evaluate the contribution of an aroma component to the retronasal aroma upon consuming a food or beverage product, a method has been proposed which includes calculating the cumulative concentration value ($C_R$) of the retronasal aroma when the food or beverage product is consumed, estimating the retronasal threshold cumulative concentration value ($C_T$) at the threshold of whether or not the aroma is perceived when the food or beverage product is consumed, and evaluating the contribution ($C_R/C_T$) using these values (see Patent literature 3).

$C_R$ after swallowing a food or beverage product is derived from the equation $C_R = a * t^{-b}$, $C_T$ is derived from the proportional relationship with the initial amount a, and two factors (a, b) are used which are related to the retronasal aroma behavior that decreases in a power functional manner after swallowing the food or beverage product.

CITATION LIST

Patent Literature

Patent literature 1: Japanese Unexamined Patent Application Publication No. 2009-031138
Patent literature 2: Japanese Unexamined Patent Application Publication No. 2019-045243
Patent literature 3: Japanese Unexamined Patent Application Publication No. 2018-141741

Non-Patent Literature

Non-patent literature 1: J. Agric. Food Chem. (2005), 53, 1700-1706

SUMMARY OF INVENTION

Technical Problem

An objective evaluation of the behavior of a retronasal aroma when a food or beverage product is consumed and a useful index for the preparation of a flavor composition for food or beverage products are required. It is desirable to be able to control the retronasal aroma when a food or beverage product is consumed by preparing a flavor composition for food or beverage products based on the results of an objective evaluation of the behavior of the retronasal aroma when the food or beverage product is consumed.

Solution to Problem

The present inventor first analyzed, continuously in real time, the aroma components that are exhaled from the mouth through the posterior nasal cavity and out of the nose (retronasal aroma) when a food or beverage product is consumed. Specifically, PTR-TOFMS (proton transfer reaction time-of-flight mass spectrometry) was used to measure the change in the concentration of each aroma component with respect to the number of breaths during a breath cycle, and the area under the curve for each number of breaths was determined.

After swallowing a certain amount of a food or beverage product, the area under the curve of retronasal aroma decreases with time, and the decay of the area under the curve with respect to the number of breaths can be approximated by a power function. Among the factors of the power function ($C = a * t^{-b}$), t is the number of breaths, a is the area under the curve for the first breath, and b is the decay coefficient. Value a is almost proportional to the amount of the aroma component added, while value b is almost independent of the amount of the aroma component added.

Values a and values b obtained above are generally unique to each aroma component in the retronasal aroma and they are parameters that indicate the behavior of each aroma component, so they can be used as indices to control the expression of the retronasal aroma from a food or beverage product when formulating a flavor composition of interest. Furthermore, by comparing each parameter of two or more aroma components and obtaining a relative magnitude relationship for each parameter, it is possible to use the relative magnitude relationship as an index to determine which aroma component affects the aromatic impression of interest more effectively.

According to a preferred aspect of the invention, since values a and values b obtained above are calculated from the results of an analysis performed by directly introducing the breath exhaled from the nose into an analyzer without the aid of an adsorbent or the like, it is easier to reflect the behavior of the retronasal aroma that is actually perceived by human.

As mentioned above, the present invention focuses on the differences between aroma components with respect to the behavior of the retronasal aroma when a food or beverage product is consumed. Thus, the present invention relates to the following: a method for evaluating aroma components; a method for preparing a flavor composition comprising the steps of evaluating aroma components by the above evaluation method and adjusting a blending ratio of the aroma components contained in a food or beverage product based on said evaluation; and a method for adjusting the flavor dosage of a flavor composition to a food or beverage product comprising the steps of evaluating aroma components by the above evaluation method and adjusting the blending ratio of the aroma components contained in the food or beverage product based on said evaluation.

[1] A method for evaluating the influence of aroma components contained in a food or beverage product, which are exhaled from the nose via the posterior nasal cavity when the food or beverage product is consumed (when eating or drinking the food or beverage product), on the aromatic impression, the method comprising the steps of:

1) regarding two or more aroma components contained in the food or beverage product, which are exhaled from the nose via the posterior nasal cavity when the food or beverage product is consumed, measuring change in concentration of each aroma component with respect to the number of breaths (t) during a breath cycle and approximating the area under the curve (C) for each number of breaths by a power function represented by the following equation: $C=a*t^{-b}$ to calculate the area under the curve per unit amount for the first breath (value a) and the coefficient representing the degree of decay of the area under the curve (value b);

2) obtaining the relative magnitude relationship of each of values a and values b of the two or more aroma components obtained in Step 1); and 3) evaluating the influence of the aroma components contained in the food or beverage product on the aromatic impression, using the magnitude relationship of each of values a and values b of the two or more aroma components obtained in Step 2) as an index that correlates with the magnitude relationship of the extent of the influence on the aromatic impression of the food or beverage product.

[2] The evaluation method according to [1] above, the method comprising, in Step 1), a step of determining values a and values b using a gas chromatograph or a mass spectrometer.

[3] A method for preparing a flavor composition, the method comprising the steps of:

A) evaluating the influence of aroma components contained in a food or beverage product, which are exhaled from the nose via the posterior nasal cavity when the food or beverage product is consumed, on the aromatic impression, by the evaluation method according to either one of [1] and [2] above; and B) preparing a flavor composition by adjusting the blending ratio of the aroma components contained in the food or beverage product based on the evaluation obtained in Step A).

[4] A method for adjusting the flavor dosage of a flavor composition to a food or beverage product, the method comprising the steps of:

i) evaluating the influence of aroma components contained in the food or beverage product, which are exhaled from the nose via the posterior nasal cavity when the food or beverage product is consumed, on the aromatic impression, by the evaluation method according to either one of [1] and [2] above; and ii) adjusting the flavor dosage of the flavor composition to the food or beverage product based on the evaluation obtained in Step i).

Advantageous Effects of Invention

According to the present invention, the influence of aroma components on the aromatic impression when a food or beverage product is consumed can be evaluated properly taking the actual consumption environment into account. For example, by employing an evaluation method of the present invention, it is possible to objectively evaluate the behavior of each aroma component when a food or beverage product is consumed.

According to a preferred aspect of the invention, it is easy to objectively evaluate the influence of aroma components contained in a food or beverage product on the aromatic impression, and it is possible to efficiently produce a formulated flavor with a controlled retronasal aroma.

DESCRIPTION OF EMBODIMENTS

Figure 1:
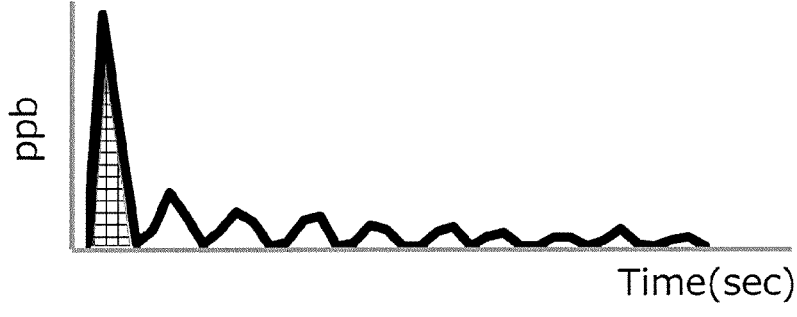
FIG. 1 is a graph schematically showing an example of the results from a measurement of change in concentration of a retronasal aroma with respect to time using a real-time measurement equipment, where the grid pattern indicates the area under the curve for the first breath.

Hereinafter, the present invention will be described in detail.

1. Method for Evaluating Aroma Components

An evaluation method of the present invention is a method for evaluating the influence of aroma components contained in a food or beverage product, which are exhaled from the nose via the posterior nasal cavity when the food or beverage product is consumed, on the aromatic impression, the method comprising the steps of:

1) regarding two or more aroma components contained in the food or beverage product, which are exhaled from the nose via the posterior nasal cavity when the food or beverage product is consumed, measuring change in concentration of each aroma component with respect to the number of breaths (t) during a breath cycle and approximating the area under the curve (C) for each number of breaths by a power function represented by the following equation: $C=a*t^{-b}$ to calculate the area under the curve per unit amount for the first breath (value a) and the coefficient representing the degree of decay of the area under the curve (value b);

2) obtaining the relative magnitude relationship of each of values a and values b of the two or more aroma components obtained in Step 1); and 3) evaluating the influence of the aroma components contained in the food or beverage product on the aromatic impression, using the magnitude relationship of each of values a and values b of the two or more aroma components obtained in Step 2) as an index that correlates with the magnitude relationship of the extent of the influence on the aromatic impression of the food or beverage product.

The evaluation method according to the present invention seeks to properly evaluate the influence of aroma components contained in a food or beverage product, which are exhaled from the nose via the posterior nasal cavity when the food or beverage product is consumed, on the aromatic impression, taking the actual consumption environment into account. Hereinafter, each of the steps will be described.

In Step 1), regarding two or more aroma components contained in a food or beverage product, which are exhaled from the nose via the posterior nasal cavity when the food or beverage product is consumed, change in concentration of each aroma component is measured with respect to the number of breaths (t) during a breath cycle, and the area under the curve (C) for each number of breaths is approximated by a power function represented by the following equation: $C=a*t^{-b}$ to calculate the area under the curve per unit amount for the first breath (value a) and the coefficient representing the degree of decay of the area under the curve (value b).

The food or beverage product is not particularly limited, but it is preferably a food or beverage product whose commercial value is enhanced by being flavored.

Examples of the beverage product include, but are not limited to, tea beverages such as green tea, powdered green tea, and black tea; soft drinks such as coffee, cocoa, carbonated drinks, fruit juices, sports drinks, and flavored water (near water); alcoholic drinks such as gin, vodka, whiskey, wine, chuhai (shochu-based alcoholic drink), sour cocktail, shochu, and sake; and beer beverages such as beer, low-malt beer, low-alcohol beer, and non-alcoholic beer.

Particularly, the beverage products to which a flavor can be added are preferred. Specifically, tea, coffee, fruit juices, sports drinks, flavored water, sour cocktails, chuhai, and beer beverages are preferred.

Moreover, examples of the food product include, but are not limited to, frozen desserts such as ice cream, sherbet, and popsicles; yogurts; Japanese and Western confectioneries; jams; candies; jellies; gums; breads; soups such as curry, stews, Japanese soups, Western soups, and Chinese soups;

flavor seasonings; various instant beverage or food product; various snack foods; nursing foods; toothpastes; and oral care products.

Among these, frozen desserts, ice creams, sherbets, yogurts, jellies, and curries are preferred. Herein, the term "food product" also includes foods that are made into a final product by mixing two or more kinds of foods.

A flavor or a flavor compound used as an aroma component in the present invention is not particularly limited, and may be any flavor contained in plants and animals that can be used as an ingredient for foods or any flavor that can be added as a food additive. Examples include flavors listed in Well-known and Customary Techniques (Flavors and Fragrances) Part II: Flavors and Fragrances for Foods, JPO Publication (Japan Patent Office), Collection of Base Materials for Natural Flavors and Fragrances (Japan Flavor and Fragrance Materials Association), and Synthetic Flavors and Fragrances (Chemical Daily Co., Ltd.).

As already mentioned, the decay of the area under the curve of retronasal aroma with respect to the number of breaths after swallowing a certain amount of food or beverage product can be approximated by a power function represented by the following equation: $C=a*t^{-b}$. According to the present invention, among the factors of the power function ($C=a*t^{-b}$), t is the number of breaths, value a is the area under the curve per unit amount for the first breath, and value b is defined as the coefficient representing the degree of decay of the area under the curve. According to the present invention, value a and value b are determined for each of two or more aroma components. Values a and values b can also be referred to as parameters of a retronasal aroma. If values a and values b cannot be obtained from an experiment or the like, computational techniques can be employed to obtain estimated values in terms of chemical structure or physical properties. Alternatively, values a and values b can be calculated using a device that can reproduce retronasal aroma behavior during consumption by human.

Note that a solvent contained in a food or beverage product, for example, a solvent contained in a flavor composition in order to dilute the formulated flavor or to increase its solubility in the food or beverage product, is not considered upon calculating each parameter since it is almost odorless by itself.

Examples of solvents that are not considered in the calculation of each parameter include: propylene glycol (propane-1,2-diol); triethyl citrate (triethyl 2-hydroxypropane-1,2,3-tricarboxylate); glyceryl acetate (1,2,3-propanetriol-triacetate) water, ethanol; and edible oils such as coconut oil and vegetable oils.

Hereinafter, embodiments of an evaluation method according to the present invention will be described in detail.

In one embodiment of the present invention, value a and value b are calculated based on the change in the actual measured concentration of each aroma component.

Figure 2:
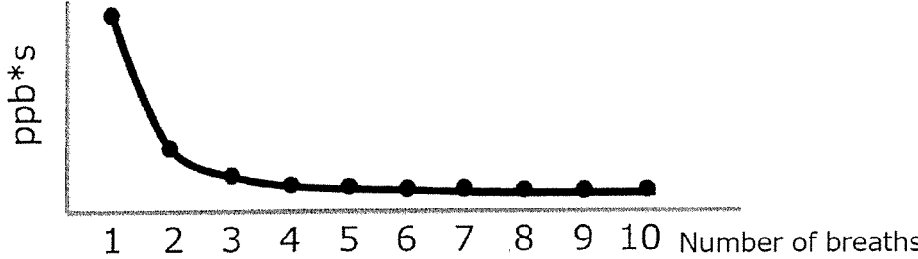
FIG. 2 is a graph schematically showing an example of a decay curve of the area under the curve of the retronasal aroma with respect to the number of breaths.

First, a food or beverage product containing an appropriate amount of one or more aroma components is swallowed, and the change in the concentration of each aroma component exhaled from the nostrils is measured in real time using PTR-TOFMS. FIG. 1 is a graph schematically showing an example of the results from a measurement of change in concentration of a retronasal aroma with respect to time using a real-time measurement equipment, where the grid pattern indicates the area under the curve for the first breath. Moreover, FIG. 2 is a graph schematically showing an example of a decay curve of the area under the curve of the retronasal aroma with respect to each number of breaths.

The change in the concentration of each aroma component is measured in real time using PTR-TOFMS to obtain a retronasal aroma curve for each number of breaths for each aroma component, as shown in FIG. 1. Based on the obtained retronasal aroma curve, the area under the retronasal aroma curve (C) is calculated for each number of breaths for each aroma component, as shown in FIG. 2. Then, the decay of the area under the curve changing with each number of breaths (t) is approximated by a power function ($C=a*t^{-b}$) to obtain the area under the curve per unit amount for the first breath (value a) and the coefficient representing the degree of decay per breath (value b). It is preferable to perform the same measurement multiple times (for example, two or more times) and average each of values a and values b over the number of measurements.

Value a is roughly proportional to the amount of the aroma component added to the food or beverage product, so it is desirable to obtain the value per unit amount by dividing by the amount added. For example, the unit of the concentration of an aroma component in the total amount of food or beverage product may be "ppm" (mass basis), in which case, value a may be expressed as a value per 1 ppm. By expressing the value per unit amount, value a can be used to represent the relative magnitude relationship among the aroma components, even if the concentrations differ among the aroma components added at the time of measurement.

The method of measuring the aroma component exhaled from the nose is not particularly limited, but a measurement and analysis can be performed efficiently by using a gas chromatograph or a mass spectrometer.

In addition, it is preferable to use real-time measurement equipment that can capture the change in the concentration of the aroma component exhaled from the nose which occurs in a short period of time. An example of such equipment is the proton transfer reaction time-of-flight mass spectrometry PTR-TOFMS (manufactured by IONICON Analytik GmbH).

For example, in the case of a beverage product, it is preferable to swallow 10 mL-30 mL at a time, which is equivalent to one sip in normal drinking. In addition, measurements from the first to tenth breaths after drinking are preferred, and measurements of at least the first to third breaths are essential.

For example, in the case of a food product, it is preferable to chew 10 g-20 g at a time, which is equivalent to one bite in normal consumption. The number of chews is not particularly limited, but it is desirable to chew the product to the extent that it can be swallowed at one time, preferably 5-30 times. The number of chews can be determined appropriately by the type of the food product for each measurement. If the same measurement is performed more than once, it should be performed under the same conditions. In addition, measurements from the first to tenth breaths after consumption are preferred, and measurements of at least the first to third breaths are essential.

As already mentioned above, in another embodiment of the present invention, a computational technique can be employed to determine estimated values of values a and values b in terms of chemical structure or physical properties.

Alternatively, in another embodiment of the present invention, instead of measuring and analyzing the aroma component exhaled from the human nose, a device that can reproduce behavior of a retronasal aroma during consumption by human may be used to measure and analyze the aroma component emitted from the device to calculate values a and values b. More specifically, a device that can reproduce behavior of a retronasal aroma during consumption by human as well as the human breath cycle, can be used to measure the change in the concentration of each aroma component emitted from the device with respect to the number of breaths during a breath cycle and determine the area under the curve for each number of breaths to calculate values a and values b in the same manner as in the previously described method.

Next, in Step 2), the relative magnitude relationship of each of values a and values b of the two or more aroma components obtained in Step 1) is obtained. Here, the term "magnitude relationship" refers to the relative magnitude relationship of each of values a and values b of the two or more aroma components.

The magnitude relationship of each of values a and values b may be relative magnitude relationship of each of values a and values b of the two or more aroma components contained in the food or beverage product. Specifically, the aroma components for which the magnitude relationship of each parameter is obtained may be at least some, and not necessarily all, of the aroma components contained in the food or beverage product. For example, the magnitude relationship can be obtained by calculating each parameter of only specific aroma components that are to be focused in terms of blending a flavor composition, such as aroma components that largely contribute to the aroma of interest or aroma components with low threshold values.

In Step 3), the influence of the aroma components contained in the food or beverage product on the aromatic impression is evaluated using the magnitude relationship of each of values a and values b of the two or more aroma components obtained in Step 2) as an index that correlates with the magnitude relationship of the extent of the influence on the aromatic impression of the food or beverage product. Here, the term "magnitude relationship" refers to the relative magnitude relationship of the extent of the influence of two or more aroma components on the aromatic impression of a food or beverage product. For example, it means that the aroma component with the higher value a of two aroma components tends to have a larger influence on the first-breath aromatic impression when the food or beverage product is consumed, while the aroma component with the lower value a of the two aroma components tends to have a smaller influence on the first-breath aromatic impression when the food or beverage product is consumed. Furthermore, it means that the aroma component with the higher value b of two aroma components shows larger decay after the second breath, while the aroma component with the lower value b of the two aroma components shows smaller decay after the second breath. Thus, an aroma component with higher value b tends to have aromatic impression that changes more quickly, while an aroma component with lower value b tends to have aromatic impression that changes less quickly.

The magnitude relationships of values a and values b, however, may not always match the magnitude relationship of the influence on the aromatic impression. A person skilled in the art can anticipate such a case and further adjust the blending ratio as necessary to obtain a flavor composition of interest.

While values a and values b of two or more aroma components are respectively compared to each other to obtain relative magnitude relationships, values a and values b may also be combined and classified into several subpopulations so as to associate each subpopulation with an index of the influence on the aromatic impression. For example, values a of aroma components belonging to a population may be separated into high and low value groups and values b may also be separated into high and low value groups so as to classify the aroma components by the combinations thereof into two to four subpopulations. Alternatively, values b can be classified into two or more subpopulations, and values a can be compared within the subpopulations to evaluate the influence on the aromatic impression. For example, it means that an aroma component that belongs to a subpopulation in which both values a and values b are high is likely to have a larger influence on the aromatic impression upon the first breath when the food or beverage product is consumed but likely to have a larger change in the aromatic impression after the second breath. On the other hand, it means that an aroma component that belongs to a subpopulation in which both values a and values b are low is likely to have a smaller influence on the aromatic impression upon the first breath when the food or beverage product is consumed but likely to have a smaller change in the aromatic impression after the second breath.

Each parameter may have different values depending on a base of a food or beverage product used as a sample. In such a case, a model base which is prepared according to the base of a targeted product is flavored with aroma components and each parameter of the aroma components is measured and compared so that the magnitude relationship of each parameter of two or more aroma components can be used as an index that correlates with the magnitude relationship of the influence on the aromatic impression perceived by human when the sample is consumed.

If the composition of the base and the measurement conditions are the same, measurements may be performed on multiple samples each having a model base flavored with different composition of aroma components, and each parameter of the two or more aroma components obtained by each measurement can be directly compared to obtain the relative magnitude relationship.

As described above, according to a preferred aspect of the invention, it is easy to objectively evaluate the influence of the aroma components contained in the food or beverage product on the aromatic impression.

According to a preferred aspect of the present invention, when formulating a flavor composition, aroma components are evaluated using the evaluation method of the present invention, and based on this evaluation, the type and blending ratio of the aroma components are selected to control the expression of the retronasal aroma according to the type and the like of the food or beverage product. According to a preferred aspect of the invention, the method for evaluating an aroma component of the present invention can be used to efficiently produce a formulated flavor with a controlled retronasal aroma.

2. Method for Preparing Flavor Composition

A method for preparing a flavor composition of the present invention comprises the steps of:

A) evaluating the influence of aroma components contained in a food or beverage product, which are exhaled from the nose via the posterior nasal cavity when the food or beverage product is consumed, on the aromatic impression, by the above evaluation method; and B) preparing a flavor composition by adjusting the blending ratio of the aroma components contained in the food or beverage product based on the evaluation obtained in Step A).

In Step A), the influence of aroma components contained in a food or beverage product, which are exhaled from the nose via the posterior nasal cavity when the food or beverage product is consumed, on the aromatic impression is evaluated by the method for evaluating aroma components according to the present invention. The method for evaluating aroma components of the present invention is already described in "1. Method for evaluating aroma components" above.

In step B), the blending ratio of the aroma components in the flavor composition used in a food or beverage product is adjusted, for example, by increasing or decreasing the relative amount of the aroma component that is found to be an aroma component with a large influence on the desired aromatic impression of the food or beverage product. According to the present invention, when a flavor composition is used in a food or beverage product, the influence on the aromatic impression of the food or beverage product can be easily controlled by increasing or decreasing the relative amount of the aroma component that is found to be an aroma component with a large influence on the desired aromatic impression of the food or beverage product.

For example, since an aroma component with relatively high value a can be evaluated to have a relatively large influence on the aromatic impression upon the first breath when the food or beverage product is consumed, it is possible to consider increasing or decreasing the blending amount of this aroma component to control the aromatic impression of the food or beverage product. Alternatively, since an aroma component with relatively low value a can be evaluated to have a small influence on the aromatic impression upon the first breath when the food or beverage product is consumed, it is possible to consider decreasing the blending amount of this aroma component or not blending the aroma component.

Moreover, for example, since an aroma component with relatively high value b can be evaluated to have aromatic impression that changes relatively large when the food or beverage product is consumed, it is possible to consider increasing the blending amount of this aroma component to make the aromatic impression of the food or beverage product last longer. On the other hand, since an aroma component with relatively low value b can be evaluated to have aromatic impression that changes relatively small when the food or beverage product is consumed, it is possible to consider decreasing the blending amount of this aroma component to make the aromatic impression thereof last shorter.

According to a preferred aspect of the present invention, the expression of a retronasal aroma when a food or beverage product is consumed is easier to control, and therefore it is possible to efficiently provide a flavor composition that expresses the desired retronasal aroma according to the type and the like of the food or beverage product. In addition, according to a preferred aspect of the present invention, it is also possible to provide a product that has more controlled retronasal aroma expression when a food or beverage product is consumed in a more efficient manner.

3. Method for Adjusting Flavor Dosage of Flavor Composition to Food or Beverage Product A method for adjusting the flavor dosage of a flavor composition to a food or beverage product according to the present invention comprises the steps of:

i) evaluating the influence of aroma components contained in the food or beverage product, which are exhaled from the nose via the posterior nasal cavity when the food or beverage product is consumed, on the aromatic impression, by the aforementioned evaluation method; and ii) preparing a flavor composition by adjusting the blending ratio of the aroma components contained in the food or beverage product based on the evaluation obtained in Step i), thereby adjusting the flavor dosage of the flavor composition to the food or beverage product.

In Step i), the influence of aroma components contained in a food or beverage product, which are exhaled from the nose via the posterior nasal cavity when the food or beverage product is consumed, on the aromatic impression is evaluated by the method for evaluating aroma components according to the present invention. The method for evaluating aroma components of the present invention is already described in "1. Method for evaluating aroma components" above.

In Step ii), the blending ratio of the aroma components in the flavor composition used in the food or beverage product is adjusted, for example, by increasing or decreasing the relative amount of the aroma component that is found to be an aroma component with a large influence on the desired aromatic impression of the food or beverage product. According to the present invention, when a flavor composition is used in a food or beverage product, it is possible to adjust the flavor dosage of the flavor composition to the food or beverage product by increasing or decreasing the relative amount of the aroma component that is found to be an aroma component with a large influence on the desired aromatic impression of the food or beverage product.

For example, if the blending amount of an aroma component with relatively high value a is high, it is possible to consider decreasing the flavor dosage of the flavor composition to control the aromatic impression of the food or beverage product. On the other hand, if the blending amount of an aroma component with relatively low value a is high, it is possible to consider increasing the flavor dosage.

If the blending amount of an aroma component with relatively high value b is high, it is possible to consider increasing the flavor dosage of the flavor composition to control the aromatic impression of the food or beverage product. Alternatively, if the blending amount of an aroma component with relatively low value b is high, it is possible to consider decreasing the flavor dosage.

According to the preferred aspect of the present invention, the expression of a retronasal aroma when a food or beverage product is consumed is easier to control, and it is possible to reduce the flavor dosage of the flavor composition to the food or beverage product by preparing a flavor composition that has a large influence on the desired aromatic impression according to the type of the food or beverage product.

EXAMPLES

Next, the present invention will be described in further detail by way of examples, but the invention is not limited to these examples. In the following examples, "%" is on a mass basis unless otherwise stated.

Aroma components contained in a food or beverage product, which are exhaled from the nose via the posterior nasal cavity when the food or beverage product is consumed, were directly introduced into a proton transfer reaction mass spectrometry "PTR-TOFMS" (manufactured by IONICON Analytik GmbH) to determine the concentration of each aroma component, which varied with each breath, from the detected ions. The main PTR-TOFMS measurement conditions are shown in Table 1.

TABLE 1

| Setting items | Input value |
|---|---|
| T-Drift (° C.) | 120 |
| Inlet Temp. (° C.) | 180 |
| FC Inlet (Sccm) | 50 |
| E/N | 90 |
| Single Spec Time (ms) | 500 |

Example 1

A standard formulated flavor composition for beverages consisting of various flavor compounds (Reference product 1) was formulated. The formulation of Reference product 1 is shown in Table 2.

TABLE 2

| <Formulation of Reference product 1> | |
|---|---|
| Name of flavor compound | Amount blended (parts by mass) |
| 2,4-Heptadienal | 0.5 |
| Allyl hexanoate | 2.0 |
| p-Cymene | 0.2 |
| Phenylacetaldehyde | 0.5 |
| 2-Hydroxy-3-methyl-2-cyclopentenone | 10.0 |
| Benzothiazole | 0.2 |
| Ethanol (solvent) | 60.6 |
| Water (solvent) | 26.0 |
| Total | 100.0 |

Reference product 1 was added to ion-exchanged water as the base at 0.1% of the total amount of the base and cooled to 5° C. to give a sample. The aroma concentrations of the flavor compounds exhaled from the nose via the posterior nasal cavity after drinking 10 mL of this sample were measured by PTR-TOFMS. The measurement time was approximately 30 seconds after drinking the sample.

The area under the curve of the concentration of each aroma component that varied during a breath cycle was calculated for each number of breaths, and the decay behavior of these values was approximated by a power function $(C = a * t^{-b})$ using the number of breaths as a variable. In the examples, value a is the area under the curve per unit amount (ppm) for the first breath, and value b is the coefficient representing the degree of decay of the area under the curve. The same measurement was performed multiple times, and the values of each parameter (a, b) was averaged over the number of measurements. The values of each parameter of the constituent flavor compounds of Reference product 1 are shown in Table 3.

TABLE 3

| Name of flavor compound | a | b |
|---|---|---|
| 2,4-Heptadienal | 1.1 | 2.9 |
| Allyl hexanoate | 2.5 | 2.9 |
| p-Cymene | 2.9 | 2.5 |
| Phenylacetaldehyde | 0.3 | 1.0 |
| 2-Hydroxy-3-methyl-2-cyclopentenone | 0.02 | 0.9 |
| Benzothiazole | 0.8 | 0.7 |

Example 2

Standard formulated flavor compositions for jellies (Reference products 2 and 3) consisting of various flavor compounds were formulated. The formulations of Reference products 2 and 3 are shown in Tables 4 and 5.

TABLE 4

<Formulation of Reference product 2>

| Name of flavor compound | Amount blended (parts by mass) |
| --- | --- |
| β-pinene | 0.5 |
| p-Tolyl acetate | 2.0 |
| Eugenol acetate | 2.0 |
| o-Aminoacetophenone | 2.0 |
| Ethanol (solvent) | 65.5 |
| Water (solvent) | 28.1 |
| Total | 100.0 |

TABLE 5

<Formulation of Reference product 3>

| Name of flavor compound | Amount blended (parts by mass) |
| --- | --- |
| Trans-2-octenal | 1.0 |
| p-Anisaldehyde | 1.0 |
| Ethanol (solvent) | 68.6 |
| Water (solvent) | 29.4 |
| Total | 100.0 |

To a base obtained by mixing 6 g of granulated sugar, 1 g of gelatin, and 50 g of ion-exchanged water through a heating process, Reference products 2 and 3 were each added at 0.3% of the total amount of the base and cooled to 5° C. to prepare samples. The aroma concentrations of flavor compounds exhaled from the nose via the posterior nasal cavity after consumption of 10 g of each sample were measured by PTR-TOFMS. The measurement time was approximately 30 seconds after the sample consumption.

For each sample, the area under the curve of the concentration of each aroma component that varied with a breath cycle was calculated for each number of breaths, and the decay behavior of these values was approximated by a power function ($C = a * t^{-b}$) using the number of breaths as a variable. For each sample, the same measurement was performed multiple times, and the values of each parameter (a, b) was averaged over the number of measurements. The values of each parameter of the constituent flavor compounds of Reference products 2 and 3 are shown in Table 6. In this example, the base flavored with Reference product 2 and the base flavored with Reference product 3 were prepared and used as samples, and, for each sample, the parameter values were each calculated based on the aroma concentrations of each constituent flavor compound. Since the composition of the base and measurement conditions were identical, the obtained parameter values can each be compared directly to obtain a relative magnitude relationship.

TABLE 6

| Name of flavor compound | a | b |
| --- | --- | --- |
| β-pinene | 1.9 | 1.8 |
| Trans-2-octenal | 0.7 | 1.4 |
| p-Tolyl acetate | 0.8 | 1.4 |
| Eugenol acetate | 0.01 | 0.8 |

TABLE 6-continued

| Name of flavor compound | a | b |
| --- | --- | --- |
| o-Aminoacetophenone | 0.02 | 0.4 |
| p-Anisaldehyde | 0.1 | 0.3 |

The following tests were then performed to verify the validity of values a and values b.

Example 3

A formulated flavor composition for beverages consisting of various flavor compounds (Standard product 1) was formulated. Regarding each parameter in a beverage, the flavor compounds in Standard product 1 were classified into those with high value a and high value b and those with low value a and low value b, and formulated flavor compositions (Comparative products 1 and 2) were formulated by changing only the amounts of the formulating compounds belonging to each group. Comparative product 1 was a formulated flavor composition in which the amounts of the formulating flavor compounds with low value a and low value b were changed, and Comparative product 2 was a formulated flavor composition in which the amounts of the formulating flavor compounds with high value a and high value b were changed. The formulations of Standard product 1 and Comparative products 1 and 2 are shown in Table 7.

TABLE 7

| Name of flavor compound | Standard product 1 | Comparative product 1 | Comparative product 2 |
| --- | --- | --- | --- |
| 2,4-Heptadienal | 0.02 | 0.02 | 0.10 |
| Allyl hexanoate | 0.02 | 0.02 | 0.10 |
| p-Cymene | 0.02 | 0.02 | 0.10 |
| Phenylacetaldehyde | 0.02 | 0.10 | 0.02 |
| 2-Hydroxy-3-methyl-2-cyclopentenone | 0.02 | 0.10 | 0.02 |
| Benzothiazole | 0.02 | 0.10 | 0.02 |
| Ethanol (solvent) | 69.92 | 69.75 | 69.75 |
| Water (solvent) | 29.96 | 29.89 | 29.89 |
| Total | 100.00 | 100.00 | 100.00 |

<Sensory Evaluation>

Five experienced panelists performed sensory evaluation for the aroma intensities upon drinking samples obtained by blending each formulated flavor composition for beverages (Standard product 1 and Comparative products 1 and 2) at 0.3% in black coffee, i.e., drip coffee diluted in water (Brix: 0.64), as the base. Evaluation was conducted at two time points: immediately after drinking (upon the first breath) and about 20 seconds after drinking (corresponding to the sixth breath). The intensity of aroma was evaluated as a relative intensity (12 levels in increments of 0.5) to that of Standard product 1. The evaluation criteria are shown below.

Evaluation Criteria
Score
6 points: Sensed very strongly
5 points: Sensed strongly
4 points: Sensed strongly to some degree
3 points: Sensed equally
2 points: Sensed weakly to some degree
1 point: Sensed weakly
0 point: Sensed very weakly Standard product 1 and each comparative product were taken as one set, and they were drunk in an order where Standard product 1 was drunk immediately before the comparative product was drunk. Evaluation was based on a system where the score was written on given evaluation paper. The simple average of the scores from the five panelists is shown in Tables 8 and 9.

TABLE 8

<Comparison of aroma intensities immediately after drinking>

| Standard product 1 | Comparative product 1 | Comparative product 2 |
|---|---|---|
| 3.0 | 4.2 | 4.6 |

TABLE 9

<Comparison of aroma intensities about 20 seconds after drinking>

| Standard product 1 | Comparative product 1 | Comparative product 2 |
|---|---|---|
| 3.0 | 4.7 | 3.2 |

Figure 3:
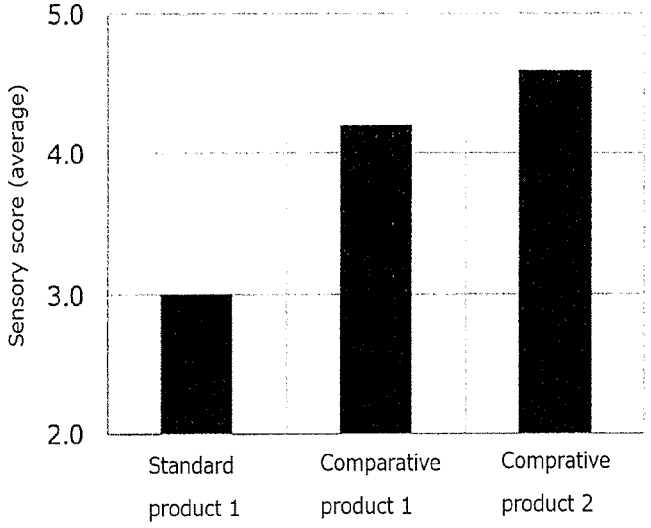
FIG. 3 shows the average scores of sensory evaluation immediately after drinking, when aroma intensities of the formulated flavor compositions for beverage obtained in Example 3 were compared.
Figure 4:
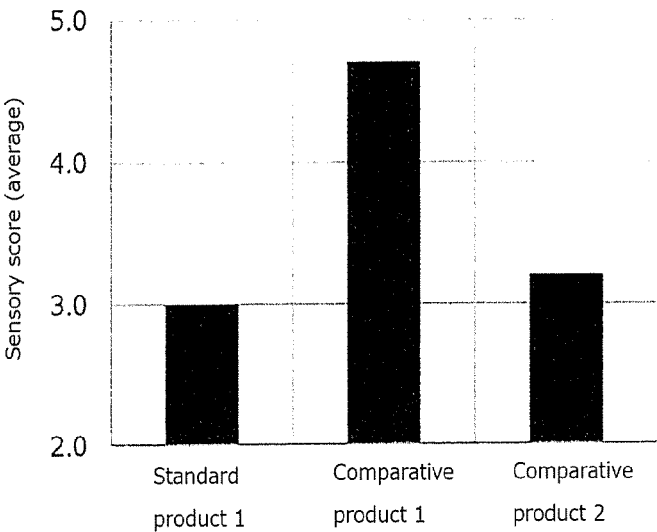
FIG. 4 shows the average scores of sensory evaluation about 20 seconds after drinking, when aroma intensities of the formulated flavor compositions for beverage obtained in Example 3 were compared.

When the aroma intensities of the comparative products were each compared to that of Standard product 1 (FIGS. 3 and 4), Comparative product 2, which contained increased amounts of flavor compounds with higher values a, showed a tendency to have a higher score immediately after drinking. Meanwhile, Comparative product 1, which contained increased amounts of flavor compounds with lower values b, showed a tendency to have a higher score about 20 seconds after drinking. This indicates that values a and values b obtained by this evaluation method were useful as indices of the influence on the aromatic impression, showing that this evaluation method is a useful method for solving the problem.

Example 4

A formulated flavor composition for jellies consisting of various flavor compounds (Standard product 2) was formulated. Regarding each parameter in a jelly, the flavor compounds in Standard product 2 were classified into those with high value a and high value b and those with low value a and low value b, and formulated flavor compositions (Comparative products 3 and 4) were formulated by changing only the amounts of the compounds belonging to each group. Comparative product 3 was a formulated flavor composition in which the amounts of the formulating flavor compounds with low value a and low value b were changed, and Comparative product 4 was a formulated flavor composition in which the amounts of the formulating flavor compounds with high value a and high value b were changed. The formulations of Standard product 2 and Comparative products 3 and 4 are shown in Table 10.

TABLE 10

| Name of flavor compound | Standard product 2 | Comparative product 3 | Comparative product 4 |
|---|---|---|---|
| β-pinene | 0.01 | 0.01 | 0.10 |
| Trans-2-octenal | 0.01 | 0.01 | 0.10 |
| p-Tolyl acetate | 0.01 | 0.01 | 0.10 |
| Eugenol acetate | 0.01 | 0.10 | 0.01 |
| o-Aminoacetophenone | 0.01 | 0.10 | 0.01 |
| p-Anisaldehyde | 0.01 | 0.10 | 0.01 |

TABLE 10-continued

| Name of flavor compound | Standard product 2 | Comparative product 3 | Comparative product 4 |
|---|---|---|---|
| Ethanol (solvent) | 69.96 | 69.77 | 69.77 |
| Water (solvent) | 29.98 | 29.90 | 29.90 |
| Total | 100.00 | 100.00 | 100.00 |

<Sensory Evaluation>

Five experienced panelists conducted a sensory evaluation of the aroma intensities upon consuming samples obtained by blending each formulated flavor composition for jellies (Standard product 2 and Comparative products 3 and 4) at 0.1% in a base made by mixing 6 g of granulated sugar, 1 g of gelatin, and 50 g of black coffee, i.e., drip coffee diluted in water (Brix: 0.64), through a heating process. Evaluation was conducted at two time points: immediately after consumption (upon the first breath) and about 20 seconds after consumption (corresponding to the sixth breath). The intensity of aroma was evaluated as a relative intensity (12 levels in increments of 0.5) to that of Standard product 2. The evaluation criteria are shown below.

Evaluation Criteria

Score 6 points: Sensed very strongly
5 points: Sensed strongly
4 points: Sensed strongly to some degree
3 points: Sensed equally
2 points: Sensed weakly to some degree
1 point: Sensed weakly
0 point: Sensed very weakly Standard product 2 and each comparative product were taken as one set, and they were consumed in an order where Standard product 2 was consumed immediately before the comparative product was consumed. Evaluation was based on a system where the score was written on given evaluation paper. The simple average of the scores from the five panelists is shown in Tables 11 and 12.

TABLE 11

<Comparison of aroma intensities immediately after consumption>

| Standard product 2 | Comparative product 3 | Comparative product 4 |
|---|---|---|
| 3.0 | 3.7 | 4.1 |

TABLE 12

<Comparison of aroma intensities about 20 seconds after consumption>

| Standard product 2 | Comparative product 3 | Comparative product 4 |
|---|---|---|
| 3.0 | 3.8 | 3.5 |

Figure 5:
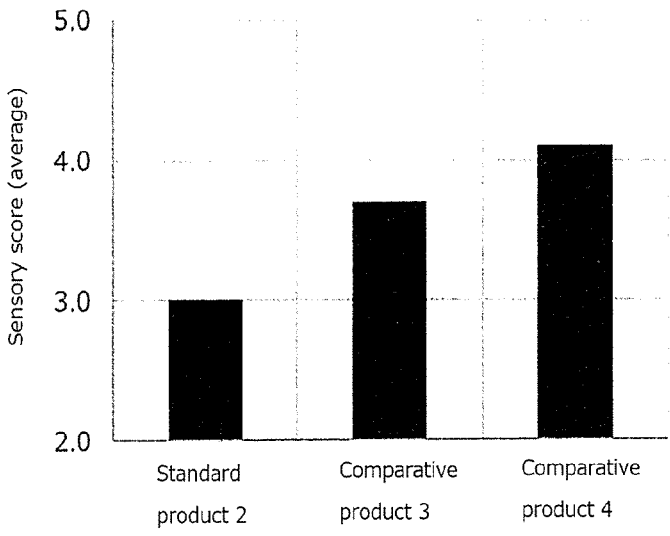
FIG. 5 shows the average scores of sensory evaluation immediately after consumption, when aroma intensities of the formulated flavor compositions for jellies obtained in Example 4 were compared.
Figure 6:
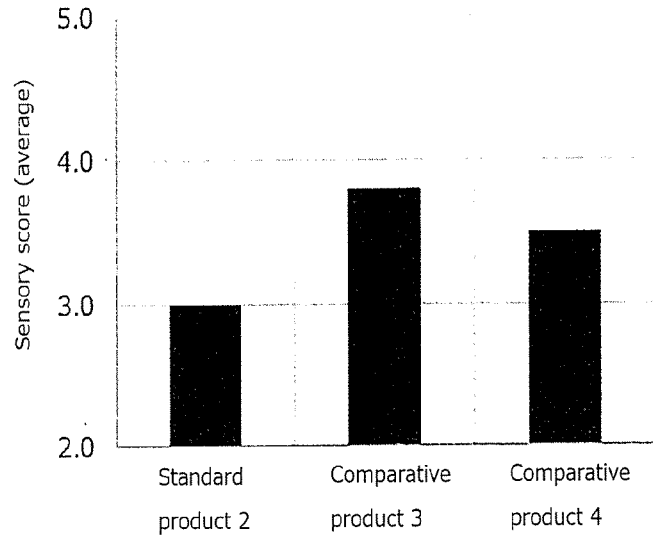
FIG. 6 shows the average scores of sensory evaluation about 20 seconds after consumption, when aroma intensities of the formulated flavor compositions for jellies obtained in Example 4 were compared.

When the aroma intensities of the comparative products were each compared to that of Standard product 2 (FIGS. 5 and 6), Comparative product 4, which contained increased amounts of flavor compounds with higher values a, showed a tendency to have a higher score immediately after consumption. Meanwhile, Comparative product 3, which contained increased amounts of flavor compounds with lower values b, showed a tendency to have a higher score about 20 seconds after consumption. This indicates that values a and values b obtained by this evaluation method were useful as indices of the influence on the aromatic impression, showing that this evaluation method is a useful method for solving the problem.

The invention claimed is:

1. A method for evaluating the influence of aroma components contained in a food or beverage product, which are exhaled from the nose via the posterior nasal cavity when the food or beverage product is consumed, on the aromatic impression, the method comprising the steps of:

1) regarding two or more aroma components contained in the food or beverage product, which are exhaled from the nose via the posterior nasal cavity when the food or beverage product is consumed, measuring change in concentration of each aroma component with respect to the number of breaths (t) during a breath cycle and approximating the area under the curve (C) for each number of breaths by a power function represented by the following equation: $C=a*t^{-b}$ to calculate the area under the curve per unit amount for the first breath (value a) and the coefficient representing the degree of decay of the area under the curve (value b);

2) obtaining the relative magnitude relationship of each of values a and values b of the two or more aroma components obtained in Step 1); and 3) evaluating the influence of the aroma components contained in the food or beverage product on the aromatic impression, using the magnitude relationship of each of values a and values b of the two or more aroma components obtained in Step 2) as an index that correlates with the magnitude relationship of the extent of the influence on the aromatic impression of the food or beverage product.

2. The evaluation method according to claim 1, the method comprising, in Step 1), a step of determining value a and value b using a gas chromatograph or a mass spectrometer.

3. A method for preparing a flavor composition, the method comprising the steps of: A) evaluating the influence of aroma components contained in a food or beverage product, which are exhaled from the nose via the posterior nasal cavity when the food or beverage product is consumed, on the aromatic impression, by the evaluation method according to claim 2; and B) preparing a flavor composition by adjusting a blending ratio of the aroma components contained in the food or beverage product based on the evaluation obtained in Step A).

4. A method for adjusting a flavor dosage of a flavor composition to a food or beverage product, the method comprising the steps of: i) evaluating the influence of aroma components contained in the food or beverage product, which are exhaled from the nose via the posterior nasal cavity when the food or beverage product is consumed, on the aromatic impression, by the evaluation method according to claim 2; and ii) adjusting the flavor dosage of the flavor composition to the food or beverage product based on the evaluation obtained in Step i).

5. A method for preparing a flavor composition, the method comprising the steps of: A) evaluating the influence of aroma components contained in a food or beverage product, which are exhaled from the nose via the posterior nasal cavity when the food or beverage product is consumed, on the aromatic impression, by the evaluation method according to claim 1; and B) preparing a flavor composition by adjusting a blending ratio of the aroma components contained in the food or beverage product based on the evaluation obtained in Step A).

6. A method for adjusting a flavor dosage of a flavor composition to a food or beverage product, the method comprising the steps of: i) evaluating the influence of aroma components contained in the food or beverage product, which are exhaled from the nose via the posterior nasal cavity when the food or beverage product is consumed, on the aromatic impression, by the evaluation method according to claim 1; and ii) adjusting the flavor dosage of the flavor composition to the food or beverage product based on the evaluation obtained in Step i).

\* \* \* \* \*